US005773006A

United States Patent [19]

Anderson et al.

[11] Patent Number: 5,773,006
[45] Date of Patent: Jun. 30, 1998

[54] LIPSOME CONTAINING IL-2

[75] Inventors: Peter M. Anderson, St. Louis Park; Arnold S. Leonard; Augusto C. Ochoa, both of Minneapolis; Cynthia Loeffler, Woodbury, all of Minn.

[73] Assignee: Regents of the University of Minnesota, Minneapolis, Minn.

[21] Appl. No.: 418,664

[22] Filed: Apr. 7, 1995

Related U.S. Application Data

[63] Continuation of Ser. No. 164,746, Dec. 10, 1993, Pat. No. 5,650,152, which is a continuation of Ser. No. 650,033, Feb. 4, 1991, abandoned, which is a division of Ser. No. 382,778, Jul. 19, 1989, abandoned, which is a continuation-in-part of Ser. No. 263,546, Oct. 27, 1988, abandoned.

[51] Int. Cl.[6] .................. A61K 45/05; A61K 39/395; A61K 39/02; A61K 39/12
[52] U.S. Cl. .............. 424/195.11; 424/423; 424/450; 424/417; 424/184.1; 424/155.1; 424/208.1; 424/234.1; 424/85.2; 424/195.1; 424/200.1; 424/812
[58] Field of Search ................ 424/184.1, 155.1, 424/208.1, 234.1, 85.2, 450, 195.1, 200.1, 812, 423, 417

[56] References Cited

U.S. PATENT DOCUMENTS

| | | | |
|---|---|---|---|
| 4,199,565 | 4/1980 | Fullerton ......................... | 424/89 |
| 4,235,877 | 11/1980 | Fullerton . | |
| 4,311,712 | 1/1982 | Evans et al. . | |
| 4,370,349 | 1/1983 | Evans et al. . | |
| 4,464,355 | 8/1984 | Fabricius et al. . | |
| 4,484,923 | 11/1984 | Amkraut et al. . | |
| 4,518,584 | 5/1985 | Mark et al. . | |
| 4,522,811 | 6/1985 | Eppstein et al. . | |
| 4,565,696 | 1/1986 | Heath et al. . | |
| 4,599,227 | 7/1986 | Dees et al. . | |
| 4,604,377 | 8/1986 | Fernandes et al. . | |
| 4,636,463 | 1/1987 | Altman et al. . | |
| 4,663,161 | 5/1987 | Mannino et al. . | |
| 4,683,199 | 7/1987 | Palladino . | |
| 4,684,625 | 8/1987 | Eppstein et al. . | |
| 4,689,222 | 8/1987 | McMichael . | |
| 4,690,915 | 9/1987 | Rosenberg . | |
| 4,721,612 | 1/1988 | Janoff et al. . | |
| 4,752,425 | 6/1988 | Martin et al. . | |
| 4,774,085 | 9/1988 | Fidler . | |
| 4,781,871 | 11/1988 | West, III et al. . | |
| 4,808,151 | 2/1989 | Dunn, Jr., et al. . | |
| 4,844,904 | 7/1989 | Hamaguchi et al. ................ | 424/85.2 |
| 4,863,740 | 9/1989 | Kissel et al. ......................... | 424/450 |
| 4,975,282 | 12/1990 | Cullis et al. . | |
| 4,983,397 | 1/1991 | Schroit et al. . | |
| 5,019,394 | 5/1991 | Hamagushi et al. . | |
| 5,023,087 | 6/1991 | Yau-Young . | |
| 5,026,557 | 6/1991 | Estis et al. ......................... | 424/450 |
| 5,100,664 | 3/1992 | Doyle et al. ......................... | 424/92 |
| 5,316,763 | 5/1994 | Ohoa . | |
| 5,650,152 | 7/1997 | Anderson et al. . | |

FOREIGN PATENT DOCUMENTS

| | | |
|---|---|---|
| 902089 | 10/1985 | Belgium . |
| 049 611 | 4/1982 | European Pat. Off. . |
| 172007 | 2/1986 | European Pat. Off. . |
| 0178 624 | 4/1986 | European Pat. Off. . |
| 0 203 403 | 12/1986 | European Pat. Off. . |
| 0 225 130 | 5/1987 | European Pat. Off. . |
| 0 240 346 | 9/1987 | European Pat. Off. . |
| 0 274 219 | 6/1988 | European Pat. Off. . |
| 62-30708 | 2/1987 | Japan . |
| 2157172 | 10/1985 | United Kingdom . |
| 85/00515 | 2/1985 | WIPO . |
| 85/00751 | 2/1985 | WIPO . |
| 85/03640 | 8/1985 | WIPO . |
| 85/03948 | 9/1985 | WIPO . |
| 87/04592 | 9/1987 | WIPO . |
| 88/00970 | 2/1988 | WIPO . |
| 89/05149 | 6/1989 | WIPO . |
| 89/05631 | 6/1989 | WIPO . |
| 89/05657 | 6/1989 | WIPO . |
| 89/09831 | 10/1989 | WIPO . |
| 89/11270 | 11/1989 | WIPO . |

OTHER PUBLICATIONS

P.M. Anderson et al., *Cancer Immunol. Immunother.*, vol. 27:82, (1988).
P.M. Anderson et al., *J. Bio. Chem.*, vol. 254:6924, (1979).
P.M. Anderson et al., *J. Immunol.*, vol. 142:1383, (1989).
P.M. Anderson et al., *Proceed. Amer. Assoc. Cancer Res.*, vol. 30:364, (1989).
P.M. Anderson et al., Abstract of Paper Presented at FASEB New Orleans, Mar. 1989 3(3):A318.
P.M. Anderson et al., *J. Cell. Biochemistry*, vol. 12, Part B, p. 255, Abstract W1OO, (1988).
N. Berinstein et al., *J. Immunol.*, vol. 140:2839, (1988).
C.G. Brooks et al., *J. Immunol.*, vol. 135:1145, (1985).
M.J. Brunda et al., *Int. J. Cancer*, vol. 37:787, (1986).
D.J.A. Crommelin et al., *Pharm. Res.*, vol. 1:159, (1984).
H.A. Fabricius et al., *Immunobiol*, vol. 156:364, (1979).
R.l. Fisher et al., *Ann. Int. Med.*, vol. 108:518, (1988).
E.A. Forssen et al., *Cancer Res.*, vol. 43:546, (1983).
J.H. Frenster et al., in *Proc. 5th Leukocyte Culture Conference*, J.E. Harris, ed. p. 359. (1970).
C.J. Froelich et al., *J. Immunol. Meth.*, vol. 86:205, (1986).
J. Fujita, *Eur. J. Cancer Clin. Oncol.*, vol. 22:445, (1986).
S. Gillis et al., *J. Immunol.*, vol. 120:2027, (1978).
M.F. Good et al., *J. Immunol.*, vol. 141:972, (1988).
R.E. Gordon et al., *Drug Dev. Ind. Pharm.*, vol. 8:465, (1982).
G. Gregoriadis and A.C. Allison, eds., *Liposomes in Biological Systems*, John Wiley & Sons, New York pp. 153–178, (1980).
E.A. Grimm et al., *J. Exp. Med.*, vol. 158:1356, (1983).
E.A. Grimm et al., *J. Exp. Med.*, vol. 157:884, (1983).

(List continued on next page.)

*Primary Examiner*—Nita Minnifield
*Attorney, Agent, or Firm*—Foley & Lardner

[57] ABSTRACT

The present invention provides a liposome comprising an effective immunoadjuvant amount of a lymphokine such as IL-2. Also provided is an effective antineoplastic amount of IL-2 liposomes in combination with adoptively transferred cells stimulated with anti-CD3 monoclonal antibody plus IL-2.

4 Claims, 3 Drawing Sheets

OTHER PUBLICATIONS

H.H. Hsieh et al., *Transplantation Proceedings,* vol. XVII:1397, (1985).
K.J. Hwang, "Liposomes From Biophysics To Therapeutics", *M.J. Ospro, ed.,* Marcel Decker, New York, pp. 109–156, (1987).
K. Itoh et al., *J. Immunol.,* vol. 134:3124, (1985).
K. Itoh et al., *J. Immunol.,* vol. 136:3910, (1986).
E.M. Janis et al., *Science,* vol. 244:713, (1989).
M. Kende et al., *Antimicrobial Agents And Chemotherapy,* vol. 27:903, (1985).
H. Konno et al., *Chemical Abstracts,* vol. 110, No. 19, p. 624, (1989), Abstract No. 171523s.
S.S. Kulkarni et al., *Annals of The New York Academy of Sciences,* vol. 507:344, (1987).
O. Leo et al., *Proc. Natl. Acad. Sci. USA,* vol. 84:1374, (1987).
G. Lopez–Berestein, *Ann. Int. Med.,* vol. 105:130, (1986).
M. Malkovsky et al., *Nature,* vol. 325:262, (1987).
S.C. Meuer et al., *Proc. Natl. Acad. Sci. USA,* vol. 81:1509, (1984).
S. Miescher et al., *J. Immunol.,* vol. 136:1899, (1986).
J.J. Mule et al., *Science,* vol. 225:1487, (1984).
L.M. Muul et al., *J. Immunol.,* vol. 138:989, (1987).
L.M. Muul et al., *J. Immunol. Meth.,* vol. 88:265, (1986).
J.H. Nunberg et al., *J. Cell. Biochem.,* Supp. 128, p. 12, (1988).
A.C. Ochoa et al., *Cancer Res.,* vol. 49:963, (1989).
A.C. Ochoa et al., *J. Immunol.,* vol. 138:2728, (1987).
J.R. Ortaldo et al., *Int. J. Cancer,* vol. 31:285, (1983).
G. Poste et al., *Cancer Research,* vol. 39:881, (1979).
M.J. Poznansky and R.L. Juliano, *Pharmacol. Rev.,* vol. 36:277, (1984).
H. Rabinowich et al., *Cancer Res.,* vol. 47:173, (1987).
A. Rahman et al., *Cancer Res.,* vol. 42:1817, (1982).
S.A. Rosenberg, "Important Advances In Oncology", V.T. DeVita et al., eds., J.P. Lippincott Co., Philadelphia, Pennsylvania, pp. 217–257, (1988).
S.A. Rosenberg et al., *J. Immunol.,* vol. 121:1951, (1978).
S.A. Rosenberg et al., *Adv. Cancer Res.,* vol. 25:323, (1977).
S.A. Rosenberg et al., *Ann. Int. Med.,* vol. 108:853, (1988).
S.A. Rosenberg et al., *Ann. of Surg.,* vol. 208:121, (1988).
S.A. Rosenberg et al., *N. Engl. J. Med.,* vol. 313:1485, (1985).
S.A. Rosenberg et al., *N. Engl J. Med.,* vol. 316:889, (1987).
S.A. Rosenberg et al., *Science,* vol. 233:1318, (1986).
D.G. Russell et al., *J. Immunol.,* vol. 140:1274, (1988).
B.E. Ryman et al., *Essays in Biochemistry,* vol. 16:49, (1980).
R.R. Salup et al., *Cancer Immunol. Immunother.,* vol. 22:31, (1986).
R. Schwab et al., *J. Immunol.,* vol. 135:1714, (1985).
S. Shu et al., *J. Immunol.,* vol. 136:3891, (1986).
S. Shu et al., *J. Immunol.,* vol. 135:2895, (1985).
K.A. Smith, *Science,* vol. 240:1169, (1988).
S. Sone et al., *Cell Immunol.,* vol. 57:42, (1981).
S. Sone et al., *J. Immunol.,* vol. 125:2454, (1980).
G. Strauss at al., *Proc. Natl. Acad. Sci. USA,* vol. 83:2422, (1986).
G. Strauss et al., *Biochem. Biophys. Acta.,* vol. 858:169, (1986).
J.L. Strausser et al., *J. Immunol.,* vol. 121:1491, (1978).
A.B. Stavitsky, *J. Immunol.,* vol. 72:360, (1954).
L. Tan et al., *Biochemical Society Transactions,* vol. 17:693, (1989).
V. Von Fliedner et al., "Progress in Chemical And Biological Research: Cellular Immunotherapy of Cancer", vol.244:223, (1987).
B.M. Vose, *Int. J. Cancer,* vol. 30:135, (1982).
A. Weinberg et al., *J. Immunol.,* vol. 140:294, (1988).
A. Weiss et al., *J. Clin. Immunol.,* vol. 4:165, (1984).
T.L. Whiteside et al., *Int. J. Cancer,* vol. 37:803, (1986).
J.M. Williams et al., *J. Immunol.,* vol. 135:2249, (1985).
J.M. Zarling et al., *Nature,* vol. 274:269, (1978).
S.C. Yang et al., *Proc. Annu. Meet. Am. Assoc. Cancer Res.,* vol. 29, (1988), Abstract No. A1603, (Meeting Abstract).
Y.P. Yen et al., *Proc. Annu. Meet. Am. Assoc. Cancer Res.,* vol. 28, (1987), Abstract No. 403, (Meeting Abstract).
Y.P. Yen et al., *Proc. Annu. Meet. Am. Assoc. Cancer Res.,* vol. 29, (1988), Abstract No. A1616, (Meeting Abstract).
J.M. Zarling et al., *Cancer Immunol. Immunother.,* vol. 15:237, (1983).
FLIER et al., "Vaccines Against Human Immunodeficiency Virus–Progress And Prospects", *New England J. Medicine,* vol. 239(19):1400–05, (1993).
Koff et al., "Development and Testing of AIDS Vaccines", *Science,* vol. 241:426–432, (1988).
Schild et al., "Human Immunodeficiency Virus And AIDS: Challenges And Progress", *The Lancet,* vol. 335:1081–84, (1990).
Ho et al. 1992. Vaccine. 10(4):209–13.
Mbawuike et al. 1990. Vaccine 8:347–352.
Anderson et al. 1994 Cytokine 6(1):92–101.

LIPSOME CONTAINING IL-2

This application is a continuation of application Ser. No. 08/164,746, filed on Dec. 10, 1993, now U.S. Pat. No. 5,650,152, issued Jul. 22, 1994, which is a continuation of application Ser. No. 07/650,033, filed Feb. 4, 1991 (now abandoned), which is a division of application Ser. No. 07/382,778, filed Jul. 19, 1989 (now abandoned), which is a continuation-in-part of application Ser. No. 07/263,546, filed Oct. 27, 1988 (now abandoned).

FIELD OF THE INVENTION

The present invention concerns liposomes containing an effective immunoadjuvant and/or antineoplastic amount of a lymphokine such as interleukin-2 (IL-2).

Background of the Invention

The utility of immunoadjuvants (or "adjuvants") in the administration of immunogenic substances has long been recognized, and considerable work has been done to discover substances which, when added to an antigen or other immunogenic substance, would potentiate antigenic activity and thereby antibody stimulating capacity. To date, many such adjuvants have been discovered, such as the use of alum precipitation of antigens; combining certain specific antigens, some of which would potentiate the activity of the others in the mixture; the use of calcium phosphate, particularly to potentiate influenza antibody production, and the similar use of Staphylococcus toxin, which appears to improve the antibody response to certain antigens. Several other adjuvant substances also have been considered such as tapioca, calcium or magnesium salts, tannin, and the like, which when added to certain specific antigens can increase the antibody titer over that obtainable when the antigen alone is administered.

Immunoadjuvants increase the amount of antibody produced and reduce the quantity of antigen necessary for injection and thus, the frequency of injection. Aluminum adjuvants are widely used, and although considered safe in man, sterile abscesses and persistent nodules may follow their use. Complete Freund's adjuvant, an oil-in-water emulsion containing tubercle bacilli, is more potent than the aluminum adjuvants. However, the deleterious side effects, including severe granuloma formation, allergic responses, and oil retention in the tissues, preclude its use in man.

Interleukin-2 (IL-2) occupies a central role in the augmentation of cell mediated immune responses. See K. A. Smith, Science, 240, 1169 (1988). It has recently been demonstrated that when used as a vaccine adjuvant, IL-2 overcomes genetic nonresponsiveness to malaria sporozoite peptides and enhances protection against Herpes simplex and rabies viruses. See, for example, M. F. Good et al., J. Immunol., 141, 972 (1988); A. Weinberg et al., J. Immunol., 140, 294 (1988); J. H. Nunberg et al., J. Cell. Biochem., supp 128, 12 (1988). IL-2 also facilitates nonspecific tumor killing by activated macrophages, and induction of the lymphokine activated killer (LAK) phenomenon in lymphocytes. See, for example, M. Malkovsky et al., Nature, 325, 262 (1987); E. A. Grimm et al., J. Exp. Med., 158, 1356 (1988); J. J. Mule et al., Science, 225, 1487 (1984); and J. M. Zarling et al., Nature, 274, 269 (1978). It has exhibited antineoplastic activity in numerous murine tumor models when used alone or in combination with adoptively transferred cells, i.e., cells stimulated with. IL-2 that exhibit lymphokine activated killer (LAK) activity. However, when this lymphokine has been utilized alone or in combination with peripheral blood mononuclear cells stimulated with IL-2 in tissue culture media, there has been limited success in human cancer immunotherapy protocols. See R. R. Salup et al., Cancer Immunol. Immunother., 22, 31 (1986); N. Berinstein et al., J. Immunol., 140, 2839 (1988); S. A. Rosenberg et al., N. Engl. J. Med., 313, 1485 (1985); ibid., 316, 889 (1987); Ann. of Surg., 208, 121 (1988), Ann. Int. Med., 108, 853 (1988); and R. I. Fisher et al., Ann. Int. Med., 108, 518 (1988). The clinical responses of patients receiving IL-2 and/or adoptively transferred cells stimulated with IL-2 have been in the range of about 20% to 30% for renal cell carcinoma, 10% to 20% for melanoma, and 15% or less for colon carcinoma.

Severe systemic toxicity has been associated with high dose, prolonged IL-2 administration in man and with protocols utilizing adoptively transferred cells with LAK activity in combination with IL-2. Side effects have included fever, malaise, hepatic and renal dysfunction, central nervous system adverse effects such as somnolence, disorientation, and coma, and anasarca associated with a life-threatening pulmonary capillary leak syndrome. See S. A. Rosenberg, in Important Advances in Oncology, V. T. DeVita et al., eds., J. P. Lippincott Co., Philadelphia, PA (1988) at pages 217–257. Furthermore, the half-life of IL-2 in vivo is only about 4 minutes.

The MC-38 murine colon adenocarcinoma, induced by subcutaneous injections of dimethylhydrazine in syngeneic C57BL/6 mice, has been used to evaluate therapeutic efficacy of immunotherapy treatment regimens against hepatic metastases of colon cancer. Significant tumor reduction in this model has been previously achieved with IL-2 activated tumor-infiltrating lymphocytes (TIL), a subpopulation of lymphocytes that infiltrate into growing cancers, in combination with IL-2 and cyclophosphamide. See S. A. Rosenberg et al., Science, 233, 1318 (1986). High doses of IL-2 alone, however, have no significant therapeutic effect on this tumor. Furthermore, a larger number of LAK cells are required to achieve tumor reduction when compared to the number of TIL cells required. Since expansion of both types of cell cultures is difficult, large numbers of cells in starting cultures, or prolonged culture times, are required in order to obtain sufficient numbers of cells for effective immunotherapy.

Liposomes, phospholipid vesicles with either one or more bilayers, profoundly modify and alter the absorption and distribution of entrapped drugs by virtue of lymphatic absorption and macrophage uptake. This uptake occurs mainly in the liver and to a lesser extent in other tissues rich in macrophages including lung, bone marrow, and spleen. See K. J. Hwang, in Liposomes from Biophysics to Therapeutics, M. J. Ostro, ed., Marcel Decker, N.Y. (1987) at pages 109–156. For example, it has been reported that the antifungal efficacy is increased and the systemic toxicity of amphotericin B is significantly reduced in a liposomal formulation. See G. Lopez-Berestein, Ann. Int. Med., 105, 130 (1986). However, the effect of liposomal incorporation and delivery on the localization and activity of cytokines and other bioactive compounds is highly unpredictable. Furthermore, liposomal stability may be adversely affected by interactions with the bioactive compound or its carrier with the phospholipid vesicle wall, leading to low levels of incorporation, leakage of the active ingredient, or low stability of the finished composition. In certain instances there is evidence that cytokine leakage from the liposomes, rather than internalization by macrophages, is associated with biologic activity.

Therefore, a continuing need exists both for immunoadjuvants of increased efficacy and reduced toxicity, as well as to improve the bioactivity and bioavailability of IL-2, while moderating its toxicity. Furthermore, a continuing need exists both for improved varieties of adoptive cells for immunotherapy of cancer and reduced toxicity associated with their use. Additionally, improvements in the drug delivery of cytokines such as IL-2 are needed in order to develop practical outpatient treatment regimens.

Brief Description of the Invention

The present invention provides a liposome comprising an effective immunoadjuvant and/or antineoplastic amount of interleukin-2 (IL-2). The present invention also provides a method to increase the immunoadjuvant and/or antineoplastic efficacy of interleukin-2 by liposomal incorporation, thus yielding an effective vaccine adjuvant or antitumor agent. For example, incorporation of IL-2 into liposomes resulted in a composition exhibiting a prolonged IL-2 half-life (68 minutes), over that exhibited by free IL-2 (about 4 minutes) in vivo, and increased antitumor efficacy in a murine pulmonary metastasis model. Significant immunoadjuvant properties of IL-2 liposomes were also demonstrated using either free or alum-adsorbed tetanus toxoid as a model antigen. These studies demonstrate the ability of liposome technology to increase the effectiveness of IL-2 and possibly of other cytokines as antineoplastic agents, and as immunoadjuvants in immunological compositions such as vaccines.

Therefore, vaccines comprising an effective adjuvant amount of the present cytokine-liposomes and an immunogenically effective amount of vaccine antigens are also within the scope of the present invention. As used herein with respect to IL-2, the term "effective immunoadjuvant amount" is defined so that a pharmaceutical unit dose of the present IL-2 liposomes exhibits a significant adjuvant effect due to the entrapped IL-2 when combined with a pharmaceutical unit dose of a vaccine antigen and a physiologically acceptable liquid vehicle to yield a finished vaccine. Thus, the level of incorporation of IL-2 in a given liposome of the invention is high enough so that the finished liquid vaccine formulation can be readily injected in an acceptable amount of a liquid vehicle. Optionally, other adjuvants such as those disclosed hereinbelow, can also be combined with the antigen and the IL-2 liposomes.

The present invention also provides an effective treatment of a variety of cancers confined to the peritoneum and/or liver using a combination of adoptively transferred cells and liposomes containing an effective antineoplastic amount of IL-2 in vivo.. These adoptively transferred cells were previously stimulated with an antibody to a lymphocyte surface receptor, such as monoclonal antibody anti-CD3, plus IL-2 (anti-CD3+IL-2) in vitro. T-cells in these in vitro cultures develop anticancer activity by a nonspecific [e.g., lymphokine activated killer (LAK)] phenomenon in which the cells are lysed in a non-MHC restricted manner. See A. C. Ochoa et al., Cancer Res., 49, 963 (1989).

Since T-cell growth is markedly augmented in the presence of monoclonal anti-CD3 antibody and IL-2, increased immune specificity against the tumor can be obtained using tumor-infiltrating lymphocytes or cells obtained after prior immunization with tumor associated antigens as starting material for anti-CD3+IL-2 stimulated cultures. It has also recently been demonstrated that $CD3^+CD4^-CD8^-$ T-cells with the gamma delta type of specific T-cell receptor have the capacity for specific antigen recognition without the requirement of major histocompatibility complex (MHC) restriction. See E. M. Janis et al., Science, 244, 713 (1989).

These cells also will rapidly expand in the presence of anti-CD3+IL-2.

As discussed above, the incorporation of IL-2 and liposomes increases the effectiveness of IL-2 as an antineoplastic agent against murine pulmonary metastases with or without adoptively transferred immune cells. In another murine model system, the MC-38 colon adenocarcinoma, the combination of adoptively transferred anti-CD3+IL-2 stimulated cells and IL-2 liposomes has proven to have significant antineoplastic effects against hepatic metastases. On the other hand, when free IL-2 is substituted using the same IL-2 dose and schedule, with or without adoptively transferred anti-CD3+IL-2 stimulated cells, no significant therapeutic benefit is seen.

Therefore, the aforementioned antineoplastic treatment comprises both 1) an effective amount of the present cytokine liposomes and 2) an effective antineoplastic amount of adoptively transferred anti-CD3+IL-2 stimulated cells. As used herein with respect to IL-2, the term "effective antineoplastic amount" is defined as a pharmaceutical unit dose of the present IL-2 liposome formulation that exhibits a significant reduction in the tumor due to the entrapped IL-2. Also, an "effective amount of adoptively transferred cells and IL-2 liposomes" is defined as the number of cells, in combination with a pharmaceutical unit dose of IL-2 liposomes, that exhibit a significant reduction in the tumor due to the combined therapy. Generally, the preferred number of cells in the treatment of humans is in the range of about $1 \times 10^8$ to $1 \times 10^{11}$ cells. The maximum dosage of IL-2 for treatment of human subjects is about $3 \times 10^6$ units per $m^2$ body surface area per day. However, if the therapeutic dose could be administered directly to the source of the tumor, the amount of IL-2 administered could be within the range of $1 \times 10^6$ to $10 \times 10^6$ units per $m^2$ body surface area per day.

The level of incorporation of IL-2 in a given liposome of the invention is high enough so that the preparation may be readily injected in viva in an acceptable amount of liquid vehicle. The route of the injection may be systemic, i.e., intravenous or subcutaneous, or local in relation to the tumor. Local injection includes, for example, injection into the tumor directly, intralymphatic, into a body cavity containing the tumor, or into the arterial bed or blood supply of the tumor. For example, for humans with hepatic tumors, the administration might be an intravenous or intraperitoneal injection, or by catheter directly into the hepatic artery.

DETAILED DESCRIPTION OF THE INVENTION

IL-2

Figure 1:
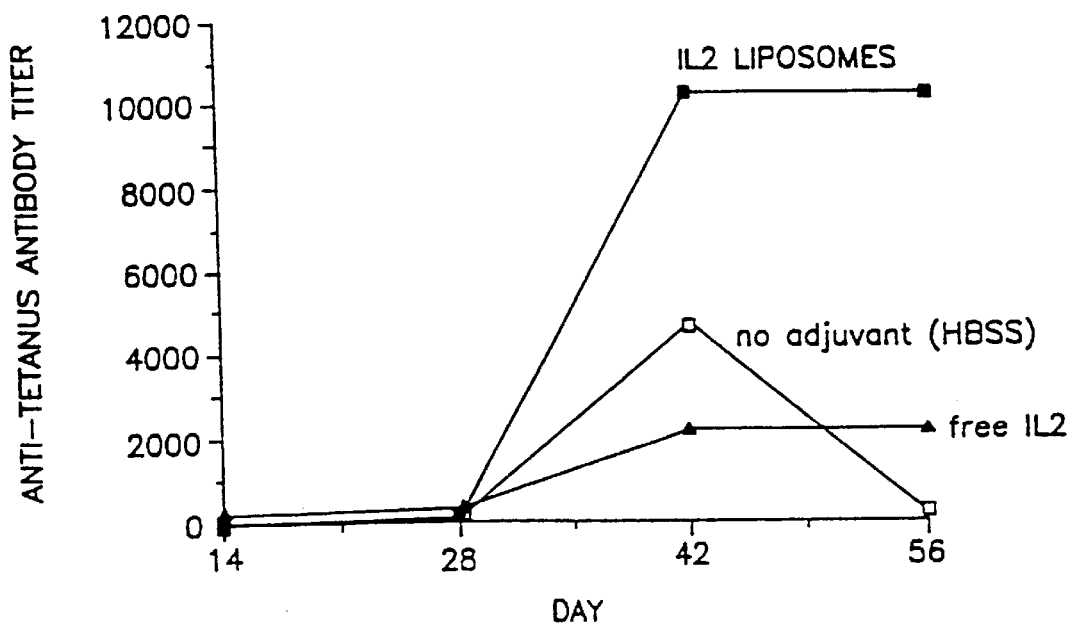
FIG. 1 is a graphical depiction of the adjuvant effect of IL-2 liposomes when used in combination with tetanus toxoid (TT).

Interleukin-2 (IL-2) is a commercially available T-cell growth factor (human interleukin-2, recombinant; T3267) and as derived from cultured rat splenocytes (T0892) from Sigma Chemical Co. (St. Louis, Mo.). Recombinant IL-2 may also be obtained from Genzyme (Boston, Mass.) or R & D Systems (Minneapolis, Minn.). It is believed that other lymphokines available to the art can also be used in the present invention. These include IL-4, IL-6, alpha interferon, and gamma-interferon. It is envisioned that these lymphokines can be used alone, in sequence, or in combination such as co-entrapment in the liposome (e.g., IL-2 and IL-6).

Liposomes

It is known that, under appropriate conditions, phospholipid dispersions can spontaneously reform, in the presence of water, into closed membrane systems. Electron microscopy reveals that these structures are made of a number of concentric bilayers of phospholipid molecules, and are called liposomes. The usefulness of liposomes as a membrane model system arises from the fact that, as the dry phospholipids undergo a defined sequence of molecular rearrangements, there is an opportunity for an unrestricted entry of hydrophilic solutes between the planes of hydrophilic head groups. Similarly, sequestration of hydrophobic solutes occurs within the hydrophobic bilayers. The result is a delivery system that can contain varying amounts of cytokines or other bioactive compounds, depending on the type of interaction between the solute and the phospholipid.

Many methods have been proposed for the preparation of liposomes. Most of these methods involve a form of aqueous hydration of the lipid, which may be either in a powdered form or as a dried film. One of the most widely used techniques is known as the film method. Briefly, lipids of the desired composition in solution with an organic solvent are dried in the form of a thin film on the walls of a round-bottomed flask. A bioactive compound can be included in the film at this stage. The dry film is hydrated by adding a suitable aqueous phase and gently swirling the flask. With a hydrophilic bioactive compound, an aqueous solution is used for hydration. The liposomes formed by this procedure generally have a number of concentric bilayers and are called multilamellar vesicles (MLVs).

Liposomes have been evaluated as potential drug delivery systems to introduce biologically active material into cells. See Poznansky and Juliano, *Pharmacol. Rev.,* 36, 277–336 (1984); B. E. Ryman et al., *Essays in Biochemistry,* 16, 49 (1980). Several routes of administration have been used for the administration of liposomes, for example, intravenous, subcutaneous, intraperitoneal, and oral delivery. See Gregoriadis and Allison, eds., *Liposomes in Biological Systems,* John Wiley & Sons, New York (1980) at pages 153–178. An important advantage of liposomal delivery is the change in tissue distribution and binding properties as compared to the free forms of the bioactive ingredient, resulting in enhanced therapeutic index and decreased toxicity. For example, decreased nephrotoxicity has been associated with the use of liposomes containing amphotericin B or cyclosporin A. See G. Lopez-Berestein, *Ann. Int. Med.,* 105, 130 (1985) and Hsieh et al., *Transplantation Proceedings,* Vol. XVII, 1397–1400 (1985). Also, reduced cardiotoxicity and nephrotoxicity are associated with liposomes containing doxorubicin and cisplatin, respectively, as compared to the free forms of the drugs. See Rahman et al., *Cancer Res.,* 42, 1817 (1982); and Forssen et al., *Cancer Res.,* 43, 546 (1983).

Although liposomes employed for delivery of bioactive agents typically range in diameter from 250 Å to several micrometers, small unilamellar vesicles (SUVs) in the range of about 250 Å to 300 Å are particularly desirable for use as drug vehicles because of their size. SUVs appear to exhibit increased partitioning to the bone marrow and also exhibit increased longevity in the circulatory system when delivered intravenously. Smaller vesicles have also been reported to be more effective in subcutaneous injections of deliver drugs to lymph nodes.

However, liposomes, including SUVs, are often unstable during long-term storage and upon infusion into mammalian systems. The reason for the lack of physical stability has not been well understood. With regard to stability within mammalian systems, however, it is known that phospholipids are substrates for enzymes such as phospholipase $A_2$, lecithin-cholesterol acyltransferase (LCAT) and the like, which are found in vivo.

Recently, W. J. Bauman in U.S. patent application Ser. No. 17,369, filed Feb. 24, 1987, disclosed a method to inhibit the phospholipase $A_2$-type cleavage of liposome membranes. In one embodiment of this invention, the phospholipase $A_2$ ($PLA_2$) hydrolysis of small unilamellar vesicle (SUV) liposomes having membranes comprising a mixture of 1-palmitoyl-2-oleoyl-sn-glycero-3-phospho-choline (POPC) and about 20–30 mol-% 1-palmitoyl-sn-glycero-3-phosphocholine (lysoPC) was completely inhibited.

Historically, liposomes have been studied as suspensions and only recently freeze-dried into a powder form to enable redispersion at the time of administration. See Gorden et al., *Drug Dev. Ind. Pharm.,* 8, 465 (1982); Crommelin et al., *Pharm. Res.,* 1, 159 (1984); and Evans et al., U.S. Pat. Nos. 4,311,712 and 4,370,349. A systematic optimization of freeze-drying of liposomes has been done in the presence of various disaccharides and cryoprotectants using carboxyfluorescein as the marker. See Fransen et al., *Int. J. Pharm.,* 33, 27 (1986).

Since liposomal instability is a major concern for long-term storage, providing liposomes in a dry powder form that is readily redispersible is highly desirable. While freeze-drying has been employed to make dry powder liposome and drug mixtures, researchers have reported problems of leakage of the drug upon reconstitution. In some cases, liposomes have been stabilized using sucrose or trehalose to maintain the integrity of liposomal membranes during freeze-drying. See Strauss & Hauser, *Proc. Natl. Acad. Sci. USA,* 83, 2422 (April 1986); and Strauss et al., *Biochim. Biophys. Acta,* 858, 169 (1986).

Vaccine Antigens

The present invention provides a potent, well-tolerated adjuvant for incorporation into a wide range of vaccines and antigen compositions for use in man and animals. The antigen itself may be in the form of purified or partially purified antigen derived from bacteria, parasites, viruses, or rickettsia, or tumor antigen, or the antigen may be an allergen such as pollens, dusts, danders, or extracts of the same, or the antigen may be in the form of a poison or a venom derived from poisonous insects or reptiles. The antigen may also be a polysaccharide or synthetic polypeptide obtained by solid phase synthesis or by the techniques of recombinant DNA. In all cases, the antigen will be in the form which, when introduced into a suitable host with or without effective adjuvant, will either induce active immunity by stimulating the production of antibodies and/or cellular immune responses against the specific antigen, or in the case of an allergen, will aid in alleviating the symptoms of the allergy due to the specific allergen. The antigens can be used either singly or in combination. Antigens of particular importance are derived from bacteria such as *H. pertussis, Leptospira pomona* and *icterohaemorrhagiae, S.* typhosa, S. paratyphi A and B, C. diphtheriae, C. tetani, C. botulinum, C. perfringens, C. feseri, and other gas gangrene bacteria, B. anthracis, P. pestis, P. multocida, V. cholerae, mycobacteria, and the like; from viruses such as poliovirus (multiple types), adenovirus (multiple types), parainfluenza virus (multiple types), measles, mumps, respiratory syncytial virus, influenza (multiple types), shipping fever virus (SF4), hepatitis B, retroviruses such as HIV and HTLVI, Western and Eastern equine encephalomyelitis, Japanese B. encephalomyelitis, Russian Spring Summer encephalomyelitis, hog cholera virus, hoof and mouth disease, fowl pox, Newcastle disease virus, rabies, feline and canine distemper, and the like; from rickettsiae as epidemic and endemic typhus or other members of the spotted fever group; from various spider and snake venoms or any of the known allergens such as ragweed, house dust, pollen extracts, grass pollens, and the like. Additional antigens of importance are derived from parasites associated with Lyme disease, malaria (plasmodium falciparum and plasmodium vivax), shistomiasis, leshmeniasis, cysticercosis (tapeworms), and flukes, or the like; and from tumor antigens derived from lung cancer, colon cancer, melanoma, and neuroblastoma.

Vaccine Formulations

The present IL-2 liposomes can be used as adjuvant supplements with commercially available vaccine formulations, or can be formulated into vaccines by combining them in an effective amount with an effective amount of the vaccine antigen preparation in a pharmaceutically acceptable, nontoxic vehicle, e.g., a liquid vehicle such as sterile, physiological saline. Delivery of the vaccine is by intramuscular, intrapleural, subcutaneous, or intradermal injection, drops or intranasal aerosol, or by a combination of these modes, at one time, or in a plurality of unit dosages.

The absolute weight of the vaccine antigen and/or the IL-2 liposomes included in a given unit dosage form of vaccine can vary widely, and depends upon factors such as the age, weight, and physical condition of the subject considered for vaccination. Such factors can be readily determined by the clinician or veterinarian employing animal models or other test systems which are well known to the art.

Stimulated Cells

Lymphocytes may be cultured in the presence of IL-2 and an antibody to a lymphocyte surface receptor. Certain monoclonal antibodies to lymphocyte surface receptors, as for example, monoclonal antibodies that bind the CD3 complex of T-lymphocytes, have mitogenic potential. Furthermore, signaling of the CD3 T-cell receptor complex results in T-cell proliferation through an interleukin-2 dependent pathway. See S. C. Meuer et al., Proc. Nat'l. Acad. Sci. USA, 81, 1509 (1984). This information has been used to produce rapidly expanding cultures of peripheral blood mononuclear cells or splenocytes with lymphokine active killer activity using the combination of lymphocytes stimulated with an antibody to a cell-surface receptor in the presence of IL-2. For example, anti-CD3 monoclonal antibodies and IL-2 ex vivo induce a large proliferation of cells in tissue culture media. See A. C. Ochoa et al., J. Immunol., 138, 2728 (1987); P. M. Anderson et al., Cancer Immunol. and Immunother., 27, 82 (1988); A. C. Ochoa, et al., Cancer Res., 49, 963 (1989); and P. M. Anderson, et al., J. Immunol., 142, 1383 (1989).

Cultures activated with the combination of anti-CD3+ IL-2 generally expand about 10 to 100 times more quickly than cultures stimulated with IL-2 alone. Furthermore, antitumor activity has been demonstrated in vivo, in the pulmonary metastatic model using MCA 106 sarcoma. However, when these anti-CD3+IL-2 activated cells are adoptively transferred to mice bearing MC-38 hepatic metastases and the animals are treated with free IL-2 once per day after cell transfer, no significant therapeutic result is seen. Surprisingly, in the presence of IL-2 liposomes, a highly significant reduction of hepatic metastases results from adoptively transferred cells previously stimulated with an antibody to a lymphocyte surface receptor plus IL-2.

The present invention will be further described by reference to the following detailed examples.

EXAMPLE 1

Preparation of IL-2-Containing Liposomes Composed of Dimyristoyl Phosphatidyl Choline in Combination With Dimyristoyl Phosphatidyl Glycerol (DMPC/DMPG)

Recombinant IL-2 with a specific activity of $3.6 \times 10^6$ units/mg protein was provided by Cetus Corporation, Emeryville, Calif. Aqueous IL-2 (1 mg IL-2/ml $H_2O$; 1 ml IL-2 solution per 300 mg lipid) was added to lipid powder which had been previously sterilized with 15,000 rad gamma irradiation from a $^{137}Cs$ source. Lipids used were dimyristoyl phosphatidyl choline (DMPC) and dimyristoyl phosphatidyl glycerol (DMPG) in a 7:3 ratio. These stable, synthetic phosphalipids were obtained from Avanti, Birmingham, Ala. and stored desiccated at $-20°$ C.

For multilamellar vesicles (MLVs) formed by hydration, the lipid/aqueous IL-2 mixture was thoroughly mixed for 1 minute using a vortex apparatus. Detergent dialysis was done using sodium chlorate, lipids and IL-2 in a 50:1 ratio; detergent was then dialyzed 36 hours with phosphate buffered saline in a LIPOSOMAL dialysis apparatus (Dianorm-Gerate, München, West Germany). This procedure is described by O. Zumbuehl et al., Biochem. Biophys. Acta, 640, 252 (1981), the disclosure of which is incorporated by reference herein. Freeze/thawing of hydrated MLVs containing IL-2 was done using three 5-minute cycles in a dry ice/propanol and 37° C. water bath.

Entrapment of IL-2 was determined by fluorescamine protein assay of the liposome pellet and supernatant of IL-2 MLV preparations centrifuged at 1000 g for 10 minutes and confirmed by gel filtration chromatography to separate free drug (MW 15,000) from the large liposomes (size 0.2 to 4 microns). The results of these studies are summarized in Table 1, below.

TABLE 1

Entrapment of IL-2 in DMPC/DMPG Liposomes

| Method | Type of Vesicle | % IL-2 Entrapment |
|---|---|---|
| (1) Hydration | Multilamellar (MLV) | 10 |
| (2) Detergent dialysis | Unilamellar | 42 |
| (3) Hydration plus freeze/thawing | Multilamellar (MLV) | 80 |

The detergent dialysis technique resulted in unilamellar vesicles with 42% IL-2 entrapped. Freeze-thawing of MLVs containing IL-2, however, resulted in 70% to 80% IL-2 protein entrapment as measured by both IL-2 bioassay and the fluorescamine protein assay. At least 95% entrapment, e.g., 95% to 98%, was obtained when lipid composition was dimyristoyl phosphatidyl choline or dipalmitoyl phosphatidyl choline alone (see Example 2). For method of IL-2 bioassay and fluorescamine protein assay see, respectively, S. Gillis et al., *J. Immunol.,* 120, 2027 (1978); and P. M. Anderson et al., *J. Biol. Chem.,* 254, 6924 (1979), both of which are incorporated by reference herein.

These results are consistent with a report that the freeze/thaw procedure increases the aqueous space available in multilamellar vesicles 5-fold to 10-fold. Liposome IL-2 preparations were stable at least three months when stored at 4° C. If made in the presence of 125 mM sucrose or trehalose, dilute IL-2 liposome preparations could be frozen without loss of vesicle contents when thawed. IL-2 liposomes could be made by the hydration and freeze/thaw technique in 30 minutes and stored at 4° C.

The liposomes may be further diluted with Hank's Balanced Salt Solution (HBSS, Sigma Chemical Co., St. Louis, Mo.) or 0.9% aqueous NaCl. For example, if a 1 mg vial of aqueous IL-2 is made into liposomes, then diluted to 3.6 ml [IL-2=$1 \times 10^6$ Cetus units/ml], this dosage can easily be administered via syringe for in vivo studies.

EXAMPLE 2

Synthesis of IL-2-Containing Liposomes Composed of Dimyristoyl Phosphatidyl Choline (DMPC)

The effects of lipid and protein concentrations, freeze/thawing, and bath sonication on the incorporation of IL-2 in lipids were evaluated using a supply of IL-2 that is free of sodium dodecyl sulfate (SDS) (unlike Cetus IL-2 used in Example 1). This recombinant IL-2 was provided by Hoffmann-LaRoche (Nutley, N.J.) with specific activity of $1.5 \times 10^7$ units/mg. Studies were done both with IL-2 containing human serum albumin (HSA) carrier (25 mg/$1 \times 10^6$ μl IL-2) and carrier free IL-2. An aqueous solution of IL-2 in Hank's Balanced Salt Solution (HBSS) was mixed with dimyristoyl phosphatidyl choline (DMPC; Avanti Polar Lipids, Pelham, Ala.; 300 mg lipid/ml of IL-2) for 1 minute using a vortex mixer, bath sonicated for 30 seconds, frozen in a dry ice/ethanol bath (5 minutes), and thawed in a 37° C. water bath (5 minutes). The DMPC had previously been sterilized with 15,000 rad gamma irradiation from a $^{137}$Cs source. After 3 cycles of freeze/thawing/sonication, the percent IL-2 in the liposome fraction was determined by CTLL-20 bioassay and fluorescamine protein assay of the liposome pellet and supernatant of preparations centrifuged at 1000 g for 10 minutes. The assays used were described previously in Example 1. See S. Gillis et al., *J. Immunol.,* supra; P. M. Anderson et al., *J. Biol. Chem.,* supra. With HSA carrier protein, the lipid to protein ratio was 2:1 and the lipid to IL-2 ratio was 750:1 in 50 mg DMPC/ml. In 300 mg DMPC/ml, the lipid to protein ratio was 12:1 and the lipid to IL-2 ratio was 4500:1. The results are summarized below in Table 2, and indicate that the liposomes in these experiments were made by a method that ensures a high concentration of IL-2 in the lipid vesicles.

TABLE 2

Incorporation of IL-2 in DMPC Liposomes

Experiment A: With Carrier Protein (HSA)

| Method | Percent IL-2 Incorporation | |
|---|---|---|
| | 50 mg DMPC/ml | 300 mg DMPC/ml |
| Hydration (vortex mixer) | 31 | 70 |
| Hydration plus freeze/thawing × 3 | 43 | 91 |
| Hydration plus freeze/thawing and bath sonication (30 sec) × 3 | 54 | 97 |

Experiment B: Without Carrier Protein

| Method | Lipid:IL-2 Ratio | % IL-2 Incorporation |
|---|---|---|
| Hydration plus freeze/thawing and bath sonication (30 sec) × 3 | 30:1 | 17.2 |
| | 100:1 | 37.5 |
| | 150:1 | 86.2 |
| | 200:1 | 94.6 |

EXAMPLE 3

Bioavailability of IL-2 in Liposomes

Bioavailability of IL-2 in the MLV, freeze/thawed liposomes of Example 1 was at least as good as the free lymphokine in an IL-2 bioassay as measured by $^3$H-thymidine incorporation into DNA of the IL-2 dependent CTLL-2 cell line. The half-life of subcutaneous IL-2 liposomes in C57BL/6 mice was 68 minutes compared to 4 minutes for the free drug. IL-2 was detectable in the serum of mice 72 hours after a single subcutaneous (sc) injection of 250,000 units of IL-2 liposomes, whereas free drug could not be detected 24 hours after injection.

EXAMPLE 4

Antitumor Activity of IL-2 in Liposomes

When the in vivo antitumor activity of IL-2 liposomes against MCA 106 sarcoma pulmonary metastases was evaluated using the intraperitoneal (ip) route in C57BL/6 mice, no therapeutic effect was seen. However, cure was achieved by local injection of IL-2 liposomes into subcutaneous tumor. Therefore, the efficacy of local [intrapleural/intrathoracic (itx)] IL-2 given as a free or liposomal formulation against pulmonary metastases was evaluated.

Groups of 8 to 10 C57BL/6 mice were housed and fed ad libitum, i.e., without restraint, according to University of Minnesota Research Animal Resources guidelines. Pulmonary metastases were induced by intravenous tail vein injection of $5 \times 10^5$ MCA 106 sarcoma cells in 0.4 cc Hank's Balanced Salt Solution (HBSS). On days 5, 6, and 7 after tumor inoculation, the mice received ether anesthesia and therapeutic injections of IL-2 by the following routes: subcutaneous (sc), nebulized, intravenous (iv), intraperitoneal (ip), or intrapleural/intrathoracic (itx). In experiment A, mice were given 50,000 units free IL-2 once per day on days 5, 6, and 7 by the sc or itx route, or 50,000 units liposomal IL-2 by the sc, iv, or itx route. The number of pulmonary metastases were enumerated on day 14 by sacrifice in a $CO_2$ gas chamber and tracheal instillation of India ink and storage of harvested lungs in Fekete's solution (300 cc 70% ethanol, 30 cc formaldehyde, 15 cc glacial acetic acid). In experiments B and C, mice received 100,000 units once per day on days 5, 6, and 7 of each of the following: free IL-2 by the ip or itx route, nebulized-free IL-2, or liposomal IL-2 by the itx route. These mice were evaluated by survival. The results are listed in Table 3 below.

TABLE 3

Effect of Local Route of Treatment in the Murine
MCA 106 Sarcoma Pulmonary Metastasis Model

| IL-2 Treatment | $N^a$ | Mean | Median | $p^b$ |
|---|---|---|---|---|
| Experiment A | | Number of Pulmonary Metastases | | |
| No therapy | 10 | 137 | 137 | — |
| sc-free IL-2 | 10 | 77 | 86 | 0.001 |
| itx-free IL-2 | 10 | 23 | 10 | 0.001 |
| iv-IL-2 liposomes | 10 | 99 | 91 | 0.097 |
| sc-IL-2 liposomes | 10 | 79 | 70 | 0.013 |
| itx-IL-2 liposomes | 10 | 11 | 6 | <0.001 |
| Experiment B | | Days Survival | | |
| No therapy | 10 | 14.7 | 14 | — |
| ip-free IL-2 | 10 | 20 | 19 | 0.691 |
| itx-free IL-2 | 10 | 16.3 | 18 | 0.084 |
| nebulized-free IL-2 | 10 | 20.3 | 19.5 | 0.017 |
| itx-IL-2 liposomes | 10 | 23 | 15 | 0.003 |
| Experiment C | | | | |
| No therapy | 10 | 17.8 | 18 | — |
| ip-free IL-2 | 10 | 17.3 | 16.5 | 0.691 |
| itx-free IL-2 | 8 | 34.5 | 26 | 0.084 |
| itx-IL-2 liposomes | 9 | 36.9 | 39 | 0.002 |

$^a$Number of mice in each group
$^b$Treatment results were compared to the control group (no therapy) using student's paired T-test (p)

As shown by the data summarized in Table 3, the itx route was significantly better than the ip, sc, or iv routes. Several experiments demonstrating the effectiveness of local routes of treatment for lung metastases were conducted and are summarized in Table 4. Pulmonary metastases were induced in groups of 8 to 10 C57BL/6 mice by intravenous tail vein injection of $5 \times 10^5$ MCA 106 sarcoma cells in 0.4 cc Hank's Balanced Salt Solution (HBSS). On days 5, 6, and 7 after tumor inoculation, the mice received ether anesthesia and therapeutic injections of IL-2 by the local itx route using free or liposomal IL-2 formulations.

In the five separate experiments reported in Table 4, IL-2 liposomes given by the itx route resulted in prolonged survival and/or fewer pulmonary metastases when compared to the free lymphokine in the murine lung metastases model.

TABLE 4

Antitumor Effect of Local IL-2
Liposomes on Pulmonary Metastases

| Treatment | IL-2 Dose/Schedule | Median | $p^b$ |
|---|---|---|---|
| Experiment 1 | | Days Survival | |
| Empty liposomes | — | 18 | — |
| Free IL-2 | 100,000 units qd × 3 | 26 | 0.084 |
| IL-2 liposomes$^a$ | 33,000 units qd × 3 | 70 | >0.001 |
| Experiment 2 | | | |
| No therapy | — | 14 | — |
| Free IL-2 | 25,000 units qd × 3 | 18 | 0.555 |
| IL-2 liposomes$^a$ | 25,000 units qd × 3 | 23.5 | 0.003 |
| Experiment 3 | | | |
| No therapy | — | 19 | — |
| Free IL-2 | 33,000 units qd × 3 | 22 | 0.001 |
| IL-2 liposomes$^a$ | 25,000 units qd × 3 | 28 | 0.001 |
| Experiment 4 | | Number of Pulmonary Metastases | |
| No therapy | — | >250 >250 | — |
| Free IL-2 | 10,000 units qd × 3 | 229 >250 | 0.091 |
| IL-2 liposomes$^a$ | 10,000 units qd × 3 | 95 44 | 0.042 |
| | | Days Survival | |
| No therapy | — | 23.7 20.5 | — |
| Free IL-2 | 30,000 units qd × 3 | 27.4 26 | 0.297 |
| IL-2 liposomes$^a$ | 30,000 units qd × 3 | 34.3 33.5 | 0.074 |
| Experiment 5 | | Number of Pulmonary Metastases | |
| No therapy | — | >250 >250 | — |
| Free IL-2 | 150,000 units day 5 100,000 units day 6 50,000 units day 7 | 107.7 68.5 | 0.008 |
| IL-2 liposomes$^a$ | 150,000 units day 5 100,000 units day 6 50,000 units day 7 | 21.3 7 | >0.001 |

$^a$Hydrated, freeze/thawed IL-2 liposomes used in all experiments
$^b$Treatment results were compared using the student's T-test compared to the control groups (no therapy)

As shown by the data summarized in Table 5, when administered by the itx route with adoptively transferred anti-CD3+IL-2 stimulated cells, an even greater reduction in the number of pulmonary metastases was seen using IL-2 liposomes. Adoptive cells were murine splenocytes stimulated and cultured in vitro eight days with anti-CD3 monoclonal antibody and IL-2. Groups of C57BL/6 mice were treated with 10,000 units local intrathoracic (itx) IL-2 as free or liposome formulation on days 5, 6, and 7 after tumor inoculation. On day 6, twenty million cells were administered itx with the IL-2 formulations.

TABLE 5

Effect of Adoptive Cells on Local ITX
IL-2 Therapy of Pulmonary Metastases

| | Number of Pulmonary Metastases | | |
|---|---|---|---|
| Treatment | Mean | Median | $p^b$ |
| No therapy | >250 | >250 | — |
| IL-2 (free drug) | 229 | >250 | 0.091 |
| IL-2 (free drug) + cells | 115 | 40 | 0.072 |
| IL-2 liposomes$^a$ | 95 | 44 | 0.042 |
| IL-2 liposomes$^a$ + cells | 76 | 35 | 0.026 |

$^a$Hydrated, freeze/thawed IL-2 liposomes
$^b$Treatment results were compared using student's T-test compared to control (no therapy) group The experiment was repeated and the results evaluated with respect to survival. Groups of mice were treated with $3 \times 10^4$ units itx IL-2, either as free or liposomal formulations, with or without adoptively transferred cells, on the same schedule as discussed above. The results are reported in Table 6.

TABLE 6

Effect of Adoptive Cells and IL-2 Liposomes on Survival

|  | Days Survival | | |
| --- | --- | --- | --- |
| Treatment | Median | sd (1σ) | p[b] |
| No therapy | 20.5 | 6.7 | — |
| IL-2 (free drug) | 26 | 7.4 | 0.297 |
| IL-2 (free drug) + cells | 28 | 12.5 | 0.155 |
| IL-2 liposomes[a] | 33.5 | 25.9 | 0.074 |
| IL-2 liposomes[a + cells] | 34.5 | 22.1 | 0.030 |

[a]Hydrated, freeze/thawed IL-2 liposomes
[b]Treatment results were compared using student's T-test compared to the control (no therapy) group Finally, an experiment was conducted to determine the dose response of IL-2. Groups of 10 C57BL/6 tumor bearing mice were treated once per day for 5 consecutive days with various doses of IL-2 using itx free IL-2 or itx liposome IL-2 formulations on days 4–8 after iv MCA-106 sarcoma tumor inoculation. The results are reported in Table 7. These results demonstrate both a dose response effect and superiority of IL-2 in liposomes compared to free IL-2 at doses of 10,000 units, 25,000 units, and 50,000 units itx for 5 consecutive days.

TABLE 7

Dose Response of Local IL-2 in Liposomes

|  | Number of MCA 106 Sarcoma Lung Metastases | | | | |
| --- | --- | --- | --- | --- | --- |
|  | IL-2 liposomes | | Free IL-2 | | |
| IL-2 Dose | Mean | sd (1σ) | Mean | sd (1σ) | p[b] |
| 10,000 units | 34.5 | 17.9 | 75.9 | 30.9 | 0.002 |
| 25,000 units | 19.9 | 13.1 | 59.8 | 20.7 | 0.001 |
| 50,000 units | 9.6 | 4.5 | 65.3 | 40.0 | 0.002 |

[a]IL-2 formulations were given by the local intrathoracic route in 0.2 cc.
[b]Comparisons of treatment results between free and liposome IL-2 formulations were done using student's T-test.

The superiority of local intrapleural (itx) IL-2 liposomes over free IL-2 is believed to be due to longer IL-2 half-life, more efficient processing of the IL-2 by macrophages, or lymphatic uptake and presentation of the lymphokine to immune cells which participate in either the LAK phenomenon or a cell mediated immune response.

In the above murine studies, no signs of toxicity, as determined by ruffled coat or decreased activity level, were observed with daily itx or ip dose regimens of liposomes containing IL-2. Canine studies with daily intrapleural IL-2 liposomes also documented acceptable toxicity when a 60 kg Irish wolfhound, after resection of a foreleg osteosarcoma, and a Great Dane were treated with up to $10 \times 10^6$ units IL-2 liposomes daily for 3 to 5 consecutive days per week through a subcutaneous port with a catheter tip in the pleural space. A 1° C. rise in temperature was observed approximately 3 hours after each dose of IL-2 liposomes. These dogs had no significant increase in respiratory rate or weight gain, and their appetites and activity levels appeared to be unaffected.

EXAMPLE 5

Adjuvant Effect of IL-2 Liposomes

A. Immunization of Mice

Since IL-2 liposomes are known to be readily taken up by macrophages, and IL-2 effects both T- and B-lymphocytes in addition to macrophages, the ability of DMPC/DMPG IL-2 liposomes of Example 1 [Table 1(3)] to function as a vaccine adjuvant was evaluated. Tetanus toxoid was chosen as a model antigen for these studies. C57BL/6 mice were given sc injections of 0.2 ml tetanus toxoid (0.8 Lf units, Connaught Lab. (Swiftwater, Pa.) mixed with no adjuvant (Hank's Balanced Salt Solution, HBSS), 33,000 units free IL-2, or 33,000 units IL-2 liposomes. A half-dose booster immunization of 0.1 ml of the same formulations was administered sc on day 28. Antibody titers were evaluated on days 14, 28, 42, and 56 using serial dilutions and the passive hemagglutination method of detection by the method of O. O. Stravitsky, *J. Immunol.*, 72, 360 (1954), the disclosure of which is incorporated by reference herein.

As shown in FIG. 1, although both free and liposome IL-2 could stimulate higher antibody titers than tetanus toxoid alone, i.e., were indeed adjuvants, only the IL-2 liposomal formulation was associated with a high, sustained rise in antibody titer as determined by passive hemagglutination.

Next, mice were immunized as described hereinabove with no adjuvant (HBSS), free IL-2, or IL-2 liposomes, and specific anti-tetanus antibody titers were determined using an ELISA assay. To conduct the ELISA, a solution of 0.6 µg/100 ml of poly-d-lysine (Sigma Chemical Co.) in aqueous carbonate buffer ($NaHCO_3$, $Na_2CO_3$; pH 9.6) was added to the wells of a 96-well assay plate and incubated for two hours at 37° C. The wells were washed five times with Dulbecco's Phosphate Buffered Saline (DPBS, GIBCO, Grand Island, N.Y.) and dried. A solution of 50% aqueous glutaraldehyde diluted to 0.5% in DPBS (100 µl/well) was incubated for 30 minutes at 37° C. and the wells were washed five times with DPBS. A 1:4 dilution of tetanus toxoid (TT) in DPBS (pH 9.6) was prepared by diluting 22.5 ml of TT stock solution (Connaught Lab.) (8 Lf units/ml), with 67.5 ml buffer. The diluted TT were added to the wells (100 µl/well) and incubated for 2 hours at 37° C. and for 18 hours at 4° C. The wells were washed five times with DPBS. A solution of sodium borohydride, 0.19 g/100 ml carbonate buffer, was added to the wells (150 µl/well) and incubated for 5 minutes at 25° C. The wells were washed five times with DPBS.

Sera from positive and negative control mice or rabbits or from animals to be tested were diluted in NFDM/DPBS (3 g NonFat Dry Milk/100 ml phosphate buffered saline plus 5 µl of 0.1% Thimersol solution/ml of NFDM/DPBS solution) and 100 µl of the diluted serum was added to each well. Incubation time was 1 hour at 37° C. (IgG) and 2 hours at 37° C. (IgM). The serum samples were removed from the wells which were then washed ten times with DPBS.

Anti-IgM (horseradish peroxidase labelled goat IgG against mouse or rabbit IgM) was diluted 1:250 in NFDM/DPBS. Anti-IgG (horseradish peroxidase labelled goat IgG against rabbit IgG or horseradish peroxidase labelled goat IgG against mouse IgG) was diluted 1:4000 in NFDM/DPBS (anti-rabbit IgG) or 1:500 for anti-mouse IgG. Incubation with these second antibodies (100 µl/well) was carried out for 1 hour at 37° C. The wells were then washed ten times with DPBS.

Substrate buffer (100 µl/well; prepared by combining 11.5 ml Tris citrate buffer, 0.0375 ml of o-phenylenediamine.2HCl, 0.01 ml of 30% $H_2O_2$, and 1 ml $H_2O$) was added to the wells and incubated for 5 minutes (rabbit IgG detection), 10 minutes (rabbit IgM detection or mouse IgG detection), or 30 minutes (mouse IgM detection) at 37° C. Stopping solution (50 μl of 53 ml 0.3 M $H_3PO_4$ plus 21 ml 0.5 M HCl diluted with water to 500 ml) was added to each well, and the absorbance (A) was determined using a 490 nm filter.

The data summarized in FIG. 2, panels A-D, confirms the superiority of the IL-2 liposomes formulation with respect to its ability to raise anti-tetanus toxoid antibody titers at days 14, 28, 42, and 56 after initial injection, respectively.

B. Immunization of Rabbits

1. Antigen Adsorption

Alum (0.05 mg) as $Al(OH)_3$ (Abello Labs., Madrid, Spain) was mixed with 1 Lf unit of tetanus toxoid (stock solution, 8 Lf units/ml, Connaught Lab.). The adsorption was carried out for 30 minutes (10 minutes rocking and 20 minutes standing at 25° C.).

2. Immunization Protocol

The immunization protocol is summarized in Table 8, below. The rabbits were injected sc at days 0 and 28 with 0.74 ml/rabbit of each of the four dosage forms.

TABLE 8

Rabbit Immunization Protocol

| Rabbit No. | Dosage form |
| --- | --- |
| 3,8 | 2 Lf alum adsorbed TT + 200,000 units of IL-2 liposomes |
| 1,2 | 2 Lf alum adsorbed TT + HBSS |
| 4,5 | 2 Lf unabsorbed TT + 200,000 units of IL-2 liposomes |
| 7,10 | 2 Lf unabsorbed TT + HBSS |

Figure 3:
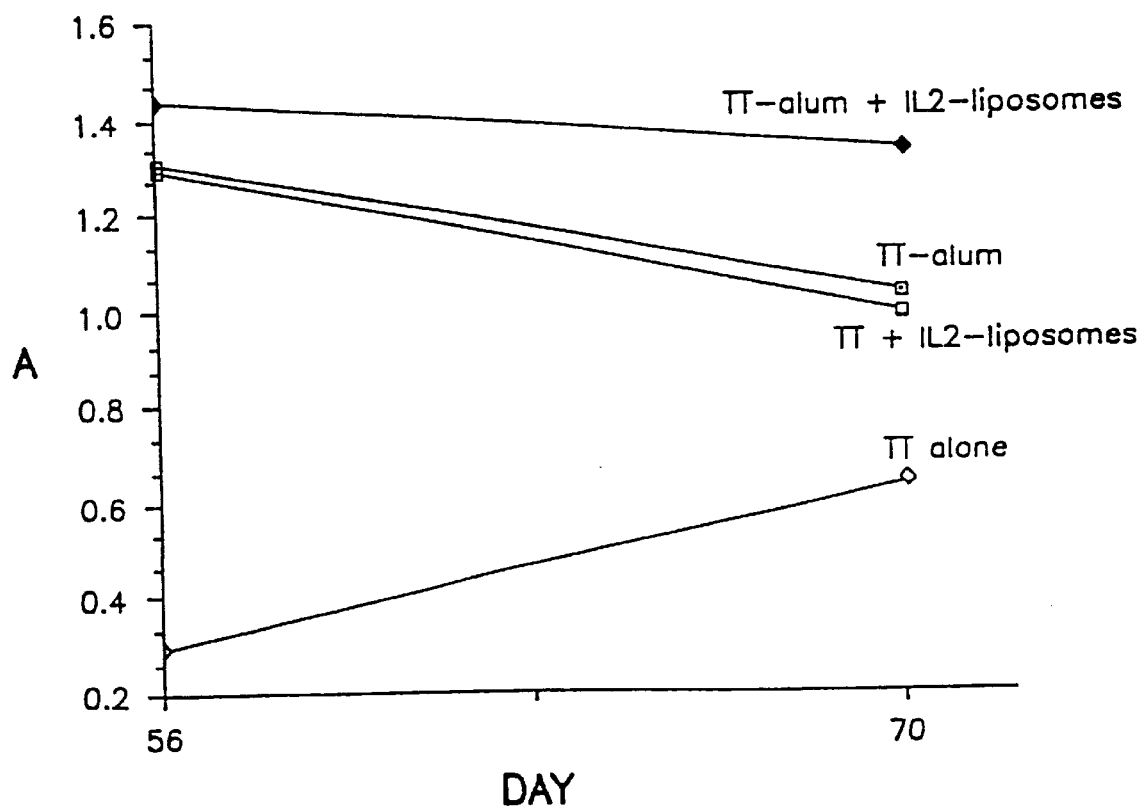
FIG. 3 is a graphical depiction of anti-tetanus IgG antibody titers attained with tetanus toxoid (TT) and alum-adsorbed TT, with and without IL-2 liposomes.
Figure 2A:
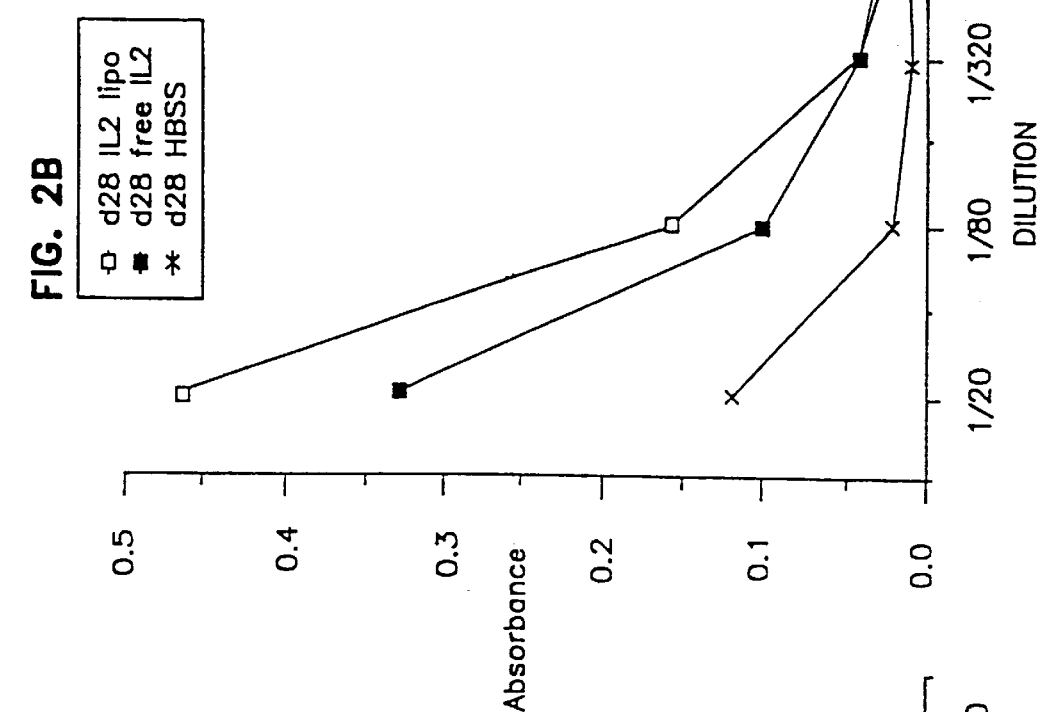
FIG. 2 (panels A-D) is a graphical depiction of anti-tetanus antibody titers attained using TT in combination with free IL-2, IL-2 liposomes (IL-2 lipo), and Hank's Balanced Salt Solution (HBSS).
Figure 2B:
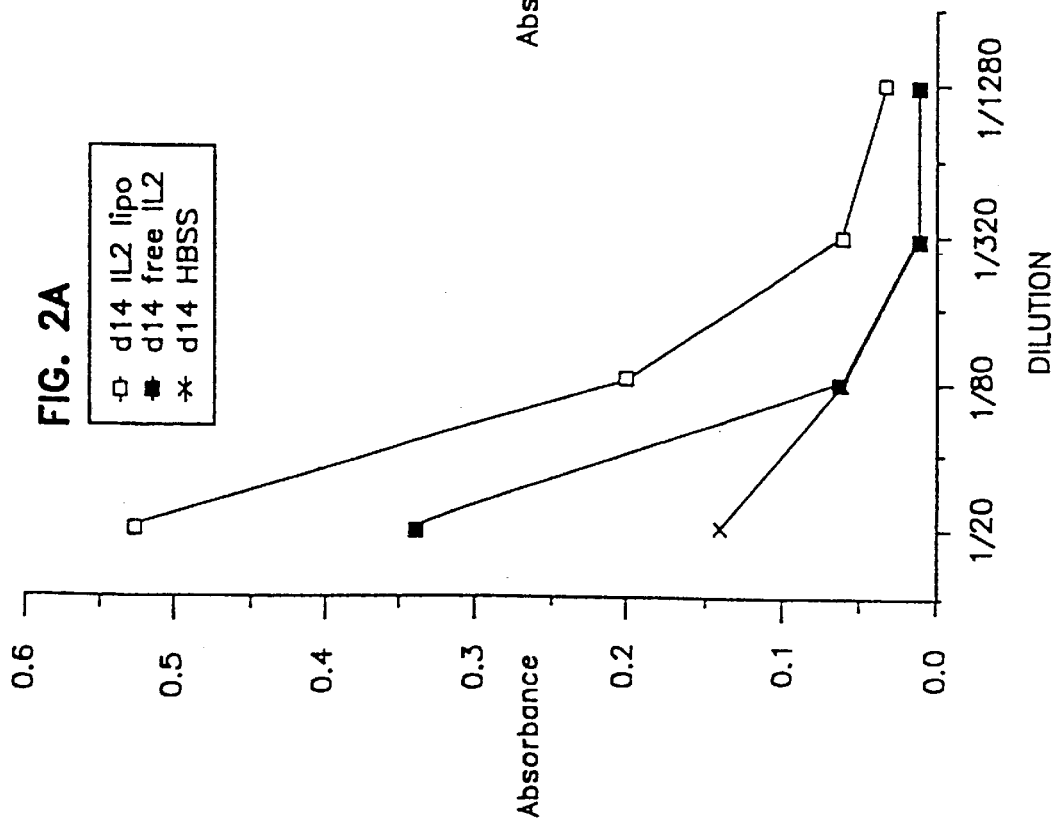
Figure 2D:
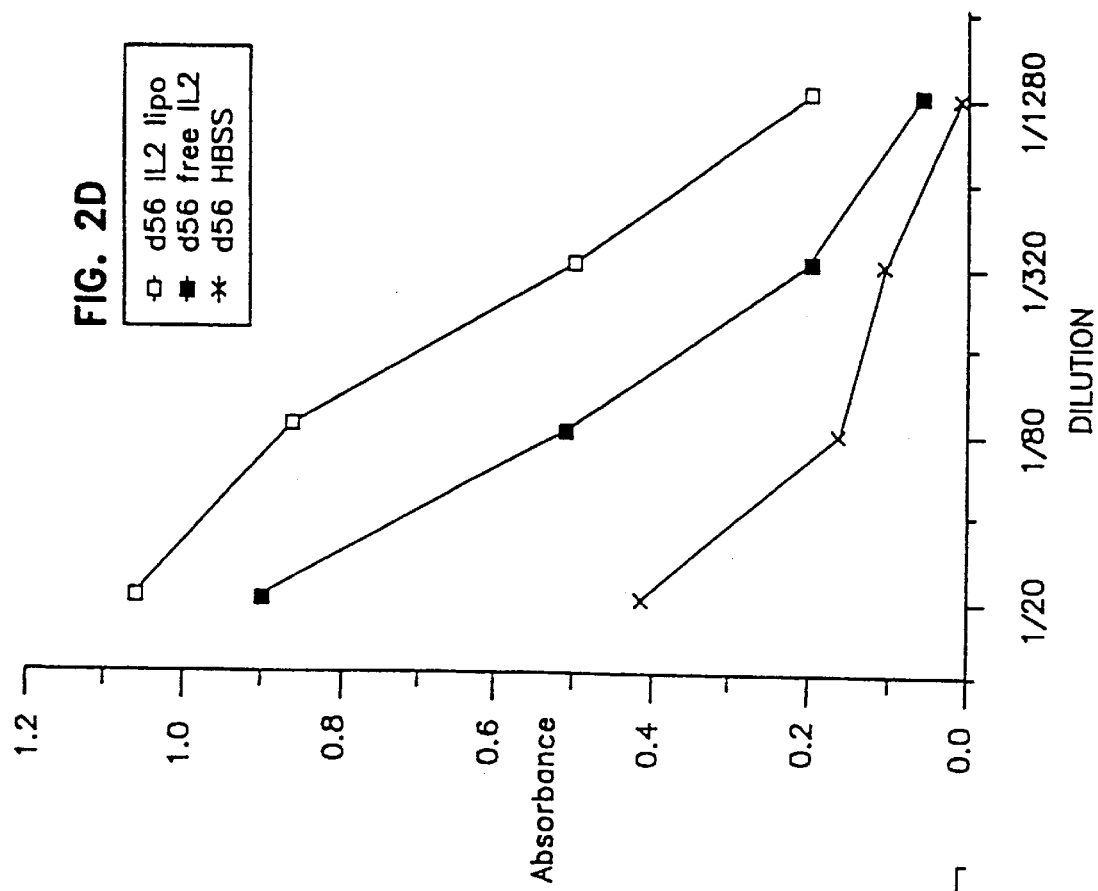
Figure 2C:
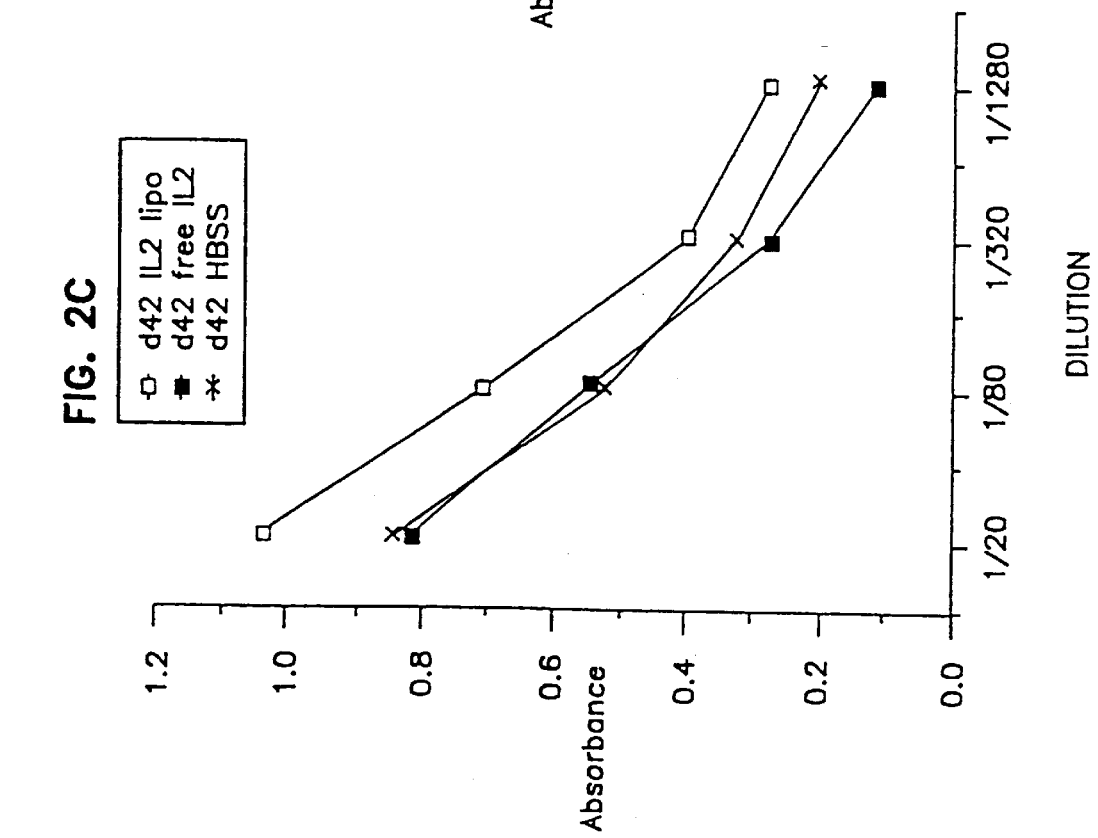

The rabbits were bled at days 56 and 70 to assay for the level and durability of the antibody response. The serum was diluted 1:80 with NFDM/DPBS and assayed via the ELISA procedure described hereinabove. The results of the assay, indicating a high and durable anti-TT antibody titer at both days 56 and 70 post-initial injection, are summarized in FIG. 3.

EXAMPLE 6

Adjuvant Effectiveness of IL-2 Liposomes when Administered to Mice in Combination with Hepatitis B Antigen Hepatitis B surface antigen (HBsAg) was provided by Merck, Inc. A/J mice were immunized with 0.1 mcg HBsAg mixed with IL-2 liposomes (50,000 units per immunization) on day 0, 5, and 19; mice received 0.05 cc into each hind footpad. Antibody titers as determined by radioimmunoassay (Abbott) indicated significantly higher antibody titers using IL-2 liposomes. Cellular immune response, as indicated by delayed type hypersensitivity (DTH), was also significantly higher when IL-2 liposomes were used. DTH to HBsAg was determined by injection of the right ear with 1 mcg HBsAg in 0.9% NaCl (0.05 cc=volume) and the left ear with 0.9% NaCl only. Ear thickness was measured 24 hours after injection using a micrometer. The results are summarized below in Table 9, and indicate a significant improvement in the immune response with inoculations of Hepatitis B/liposome IL-2 vaccine formulations as compared to Hepatitis B antigen alone.

TABLE 9

Adjuvant Effects of IL-2 Liposomes Using Hepatitis B Antigen (HBsAg)

Anti-HBsAg Antibody Titers

| Adjuvant | $N^a$ | Mean Titer $mIu^b$ | sd (1σ) | $p^c$ |
| --- | --- | --- | --- | --- |
| None (HBSS) | 4 | 2.0 | 0.9 | — |
| IL-2 liposomes | 5 | 39.3 | 19.5 | 0.007 |

DTH: Challenge with Intradermal HBsAg

| Adjuvant | $N^a$ | $M.E.T.D.^d$ | sd (1σ) | $p^1$ | $p^2$ |
| --- | --- | --- | --- | --- | --- |
| None (HBSS) | 5 | 0.018 | 0.028 | 0.221 | — |
| IL-2 liposomes | 4 | 0.095 | 0.037 | 0.014 | 0.009 |

[a]Number of mice in each group
[b]MilliInternational units of specific anti-$HB_sAg$ antibody as determined using reference standard provided in Abbott RIA kit
[c]Student's unpaired T-test;
[1]paired T-test (within group);
[2]unpaired T-test (between groups)
[d]Mean Ear Thickness Difference

EXAMPLE 7

Adjuvant Effectiveness of IL-2 Liposomes when Administered to Mice in Combination with Human Immunodeficiency Virus (HIV) Antigens Human Immunodeficiency Virus (HIV) antigens were obtained as a purified viral lysate (1 mg) from BioDesign, Inc. (Kennebunkport, Me.). The viral lysate contained small quantities of gp41 and core proteins, but no detectable gp120. Significant adjuvant effects of IL-2 liposomes on humoral and cellular immune responses in Balb C mice immunized with HIV antigens was demonstrated. Groups of 10 mice were immunized with 0.1 mcg, 0.5 mcg, and 2.5 mcg HIV antigen, mixed with HBSS or IL-2 liposomes (75,000 units per immunization) intradermally (footpad) on day 0, 7, and 21. Each hind footpad was injected with 0.05 cc after anesthesia with 1.2 mg pentobarbital. On day 33, serum was obtained from 5 mice and anti-HIV titers were determined using the Genetic Systems EIA kit. Cellular immune responses to HIV antigens were determined by injection of the right ear with 1 mcg HIV antigen in 0.9% NaCl (0.05 cc=volume) and the left ear with 0.9% NaCl only. Ear thickness was measured 24 hours after injection using a micrometer. The results are shown below in Tables 10 and 11, and indicate a significant increase in the humoral and cellular immune response with the incorporation of IL-2 liposomes in HIV vaccine formulations.

TABLE 10

Anti-HIV Humoral Immune Response Augmented by IL-2 Liposomes

| Antigen Dose (mcg) | Adjuvant | Anti-HIV $Titer^a$ Mean | sd (1σ) | $p^b$ |
| --- | --- | --- | --- | --- |
| 0.1 | HBSS (none) | 0.092 | 0.021 | |
| 0.1 | IL-2 liposomes | 0.795 | 0.281 | <0.001 |
| 0.5 | HBSS (none) | 0.233 | 0.128 | |
| 0.5 | IL-2 liposomes | 0.594 | 0.158 | <0.001 |
| 2.5 | HBSS (none) | 0.163 | 0.040 | |

TABLE 10-continued

Anti-HIV Humoral Immune Response
Augmented by IL-2 Liposomes

| Antigen Dose (mcg) | Adjuvant | Anti-HIV Titer[a] | | |
|---|---|---|---|---|
| | | Mean | sd (1σ) | p[b] |
| 2.5 | IL-2 liposomes | 1.010 | 0.314 | <0.001 |

[a]Optical density at 450 nm on Genetic Systems plate reader. Serum samples of individual mice were diluted 1:75 prior to determination of specific anti-HIV antibodies using Genetic Systems enzyme immunoassay (EIA)
[b]Student's unpaired T-test between groups of mice immunized with same dose of antigen

TABLE 11

Anti-HIV Cellular Immune Response
Augmented by IL-2 Liposomes

| Antigen Dose (mcg) | Adjuvant | M.E.T.D.[a] | sd (1σ) | p[c] | p[b] |
|---|---|---|---|---|---|
| 0.1 | HBSS (none) | 0.014 | 0.033 | 0.294 | — |
| 0.1 | IL-2 liposomes | 0.100 | 0.022 | 0.007 | 0.007 |
| 0.5 | HBSS (none) | 0.030 | 0.021 | 0.099 | — |
| 0.5 | IL-2 liposomes | 0.126 | 0.043 | 0.011 | 0.010 |

[a]Mean Ear Thickness Difference in milliliters as determined with micrometer
[b]Student's unpaired T-test between groups of mice immunized with same dose of antigen
[c]Student's paired (within group) T-test comparing HIV test ear and contralateral saline control ear

EXAMPLE 8

Culture of Anti-CD3+IL-2 Cells

Splenocytes from 6–12 weeks C57BL/6 mice were obtained by gentle crushing of spleens with sterile glass stopper and suspension of the tissue culture media consisting of RPMI 1640 supplement (GIBCO, Grand Island, N.Y.) with 25 mM HEPES, 2 mM L-glutamine, 5% fetal calf serum, 100 units per ml penicillin, 100 micrograms per ml streptomycin, 10 mM nonessential amino acids, 10 mM sodium pyruvate (GIBCO, Grand Island, N.Y.), and 25 micromolar 2-mercaptoethanol (Sigma Chemical Co., St. Louis, Mo.). Mononuclear cells obtained from splenocyte cell suspensions were filtered through Nytex screen, then centrifuged over Ficoll-Hypaque (Pharmacia, Piscataway, N.J.) to obtain a mononuclear cell preparation. Interface cells were collected and washed with tissue culture media twice and then transferred to flasks containing tissue culture media supplemented with 145-2C11, a murine anti-CD3 antibody, and IL-2 (300 units per ml). See O. Leo at al., Proc. Nat'l Acad. Sci. USA, 84, 1374 (1987). The density of the cells initially was $0.5 \times 10^6$ cells per ml. They were incubated at 37° C. in a humidified 5% $CO_2$ atmosphere. The cells were harvested on days 5, 7, and 9 and administered, i.e., adoptively transferred, using the intraperitoneal route in a volume of 0.2 cc for each tumor bearing mouse. These mice had previously received intrasplenic injections of $0.5 \times 10^6$ MC-38 colon adenocarcinoma cells on day 0 and were treated with adoptive cells ip on days 3, 5, and 7. Some mice were also treated with IL-2 liposomes once per day (doses ranging from 10,000 to 50,000 units) in 0.2 cc ip on days 3 through 7. Eleven days after tumor inoculation, the mice were evaluated for the presence of liver metastases by injection of the superior mesenteric vein with India ink and direct counting of liver metastases. Animals treated with empty liposomes, cells alone, cells plus free IL-2, or IL-2 liposomes alone had no significant reduction in the number of hepatic metastases. Only when the combination of anti-CD3+IL-2 cells and IL-2 liposomes was used, was a significant reduction in hepatic metastases seen. A dose response pattern was present for both the liposome and cellular arms of the therapy, i.e., a superior reduction in metastases was seen with increasing doses of IL-2 liposomes and cells. See Tables 12–14.

TABLE 12

Synergistic Antineoplastic Effect of
Anti-CD3 + IL-2 Stimulated Cells and IL-2 Liposomes

| | Number of MC-38 Hepatic Metastases | | |
|---|---|---|---|
| Treatment[a] | Mean | sd (1σ) | p[b] |
| Controls (empty liposomes) | 243 | 21 | NS |
| 50,000 units IL-2 liposomes | 238 | 19 | NS |
| 50 million cells × 3 (cells only) | 237 | 22 | NS |
| 50,000 units free IL-2 and 50 million cells × 3 | 235 | 58 | NS |
| 50,000 units IL-2 liposomes and 50 million cells | 28 | 33 | <0.001 |

[a]Groups of mice with MC-38 hepatic metasteses were treated once per day: on days 3 through 7 with empty liposomes (control) or IL-2 liposomes only; on days 3, 5, and 7 with cells alone; on days 3 through 7 with free IL-2 plus on days 3, 5, and 7 with cells; on days 3 through 7 with IL-2 liposomes plus on days 3, 5, and 7 with cells.
[b]Treatment results were compared using the student's T-test
NS = not significant

TABLE 13

Dose Response of IL-2 Liposomes

| | Number of MC 38 Hepatic Metastases | | |
|---|---|---|---|
| IL-2 Liposome Dose[a] | Mean | sd (1σ) | p[b] |
| Control (empty liposomes) | 210 | 44 | — |
| 10,000 units | 165 | 67 | 0.17 |
| 25,000 units | 138 | 63 | 0.02 |
| 50,000 units | 46 | 32 | 0.001 |

[a]C57BL/6 mice (groups of 10) bearing MC-38 hepatic metastases were treated with $5 \times 10^7$ anti-CD3 + IL-2 cells ip on days 3, 5, and 7 after tumor inoculation. Mice also received IL-2 in liposomes ip once per day on days 3 through 7 in dosages as shown above.
[b]Treatment results were compared using the student's T-test compared to the control group (empty liposomes).

TABLE 14

Dose Response of Anti-CD3 + IL2

| Anti-CD3 + IL-2 Stimulated Cells[a] | Number of MC-38 Hepatic Metastases | | |
|---|---|---|---|
| | Mean | sd (1σ) | p[b] |
| Controls (none) | 232 | 23 | — |
| 10 million | 204 | 39 | 0.06 |
| 25 million | 126 | 62 | >0.001 |
| 50 million | 60 | 29 | >0.001 |

[a]Mice bearing MC-38 hepatic metastases were treated once per day on days 3 through 7 with 50,000 units IL-2 liposomes ip and with adoptively transferred anti-CD3 + IL-2 stimulated cells in various numbers, as indicated in the table.
[b]Treatment results were compared using the student's T-test.

Thus, the entrapment of IL-2 liposomes results in a composition with both significant antitumor and adjuvant efficacy. Since numerous recombinant cytokines other than IL-2 are available, similar approaches using liposomes could possibly be utilized to increase the therapeutic usefulness of immune response modifying agents in both cancer and vaccine research.

The invention has been described with reference to various specific and preferred embodiments and techniques. However, it should be understood that many variations and modifications may be made while remaining within the spirit and scope of the invention. The relevant portions of the references cited herein are incorporated by reference.

What is claimed is:

1. Liposomes comprising liposomal lipid, interleukin-2 and a protein carrier, wherein the carrier:liposomal lipid ratio (w/w) is from 1:2 to 1:12, wherein said liposomal lipid is dimyristoyl phosphatidyl choline, and wherein said carrier is human serum albumin.

2. The liposomes of claim 1, wherein the liposomal lipid:interleukin-2 ratio (w/w) is from 750:1 to 4500:1.

3. The liposomes of claim 1 that have been produced by a method comprising:

(A) preparing an aqueous solution comprising interleukin-2, human serum albumin, and dimyristoyl phosphatidyl choline, (B) sonicating said solution, (C) freezing said sonicated solution, (D) thawing said frozen solution, and (E) repeating steps (B)-(D) twice to produce a final solution, wherein said final solution comprises multilamellar vesicles that contain interleukin-2.

4. The liposomes of claim 3, wherein the dimyristoyl phosphatidyl choline:interleukin-2 ratio (w/w) is from 750:1 to 4500:1.

* * * * *